US010195058B2

(12) United States Patent
Katyal et al.

(10) Patent No.: US 10,195,058 B2
(45) Date of Patent: Feb. 5, 2019

(54) HYBRID AUGMENTED REALITY MULTIMODAL OPERATION NEURAL INTEGRATION ENVIRONMENT

(71) Applicant: The Johns Hopkins University, Baltimore, MD (US)

(72) Inventors: Kapil D. Katyal, Chevy Chase, MD (US); Brock A. Wester, Baltimore, MD (US); Matthew S. Johannes, Catonsville, MD (US); Timothy G. McGee, Columbia, MD (US); Andrew J. Harris, Columbia, MD (US); Matthew Fifer, Baltimore, MD (US); Guy Hotson, Baltimore, MD (US); David McMullen, Holmdel, NJ (US); Robert S. Armiger, Catonsville, MD (US); R. Jacob Vogelstein, Bethesda, MD (US); Nathan E. Crone, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/275,029

(22) Filed: May 12, 2014

(65) Prior Publication Data
US 2014/0336781 A1    Nov. 13, 2014

Related U.S. Application Data

(60) Provisional application No. 61/822,635, filed on May 13, 2013.

(51) Int. Cl.
*A61F 2/54* (2006.01)
*A61F 2/72* (2006.01)
(Continued)

(52) U.S. Cl.
CPC .................. *A61F 2/72* (2013.01); *A61F 2/54* (2013.01); *A61F 4/00* (2013.01); *B25J 9/1697* (2013.01);
(Continued)

(58) Field of Classification Search
None
See application file for complete search history.

(56) References Cited

U.S. PATENT DOCUMENTS

| 7,628,750 B2 | 12/2009 | Cohen et al. |
| 9,445,739 B1 * | 9/2016 | Payton ................. A61B 5/0476 |

(Continued)

FOREIGN PATENT DOCUMENTS

| CN | 202533867 U | * | 11/2012 | ............... G06F 3/01 |
| JP | 2000-279435 A | * | 10/2000 | ............... A61F 2/68 |

OTHER PUBLICATIONS

JP 2000-279435A (Oct. 2000): manual or human translation.*

*Primary Examiner* — David H Willse
(74) *Attorney, Agent, or Firm* — Noah J. Hayward

(57) ABSTRACT

A method of controlling a device relative to one or more objects in an environment of a user employing the device may include receiving a volitional input from the user indicative of a task to be performed relative to an object with the device, receiving object targeting information associated with interaction between the device and the object where the object targeting information is presented in an augmented reality context, integrating the volitional input with the object targeting information to determine a control command to direct the device to interact with the object, and providing the control command to the device.

20 Claims, 3 Drawing Sheets

(51) Int. Cl.
  *B25J 9/12* (2006.01)
  *B25J 9/16* (2006.01)
  *A61F 4/00* (2006.01)
  *A61F 2/70* (2006.01)
  *A61F 2/68* (2006.01)

(52) U.S. Cl.
  CPC . *A61F 2002/6881* (2013.01); *A61F 2002/704* (2013.01)

(56) References Cited

U.S. PATENT DOCUMENTS

| | | |
|---|---|---|
| 2003/0030397 A1 | 2/2003 | Simmons |
| 2003/0093129 A1* | 5/2003 | Nicolelis .............. A61B 5/0478 607/45 |
| 2003/0120183 A1* | 6/2003 | Simmons ................ 600/595 |
| 2004/0267320 A1* | 12/2004 | Taylor ................ A61F 2/72 607/2 |
| 2005/0206583 A1 | 9/2005 | Lemelson et al. |
| 2007/0016265 A1 | 1/2007 | Davoodi et al. |
| 2008/0191864 A1 | 8/2008 | Wolfson |
| 2010/0110368 A1 | 5/2010 | Chaum |
| 2012/0257035 A1* | 10/2012 | Larsen ................ G06F 3/013 348/78 |
| 2012/0262558 A1 | 10/2012 | Boger et al. |
| 2013/0063432 A1 | 3/2013 | Kaps et al. |
| 2013/0093789 A1 | 4/2013 | Liu et al. |
| 2013/0343640 A1* | 12/2013 | Buehler ................ B25J 9/0087 382/155 |
| 2014/0031952 A1* | 1/2014 | Harshbarger ............ A61F 2/72 623/25 |

* cited by examiner

HYBRID AUGMENTED REALITY MULTIMODAL OPERATION NEURAL INTEGRATION ENVIRONMENT

CROSS-REFERENCE TO RELATED APPLICATIONS

This application claims priority to and the benefit of U.S. Provisional Application Ser. No. 61/822,635 filed on May 13, 2013, the entire content of which is hereby incorporated herein by reference.

STATEMENT OF GOVERNMENTAL INTEREST

This invention was made with government support under contract number 90045078 awarded by the National Institutes of Health (NIH). The government has certain rights in the invention.

TECHNICAL FIELD

Example embodiments generally relate to assistive devices and, more particularly, relate to a human rehabilitation/assistive device that hybridizes computer automation and human volitional control to perform everyday Activities of Daily Living (ADL) tasks.

BACKGROUND

Prosthetic devices are an example of assistive devices that have continued to evolve over time to improve the functional capabilities and aesthetic appearance. In relation to improving functional capabilities of such devices, one area in which improvement is desired relates to the use of brain-machine interfaces (BMI). BMIs attempt to provide direct communication link between the brain and the prosthetic device to assist with sensory-motor functions. However, current BMIs lack widespread clinical use due to their general inability to provide paralyzed patients reliable control of prosthetic devices to perform everyday tasks.

Some robotic prosthetic devices such as modular prosthetic limbs (MPLs) are now capable of performing a wide range of dexterous tasks. However, current BMIs tend to require daily training and a significant amount of cognitive effort to enable low-level kinematic control of multiple degrees of freedom. Accordingly, improved BMI may be desirable.

BRIEF SUMMARY OF SOME EXAMPLES

Accordingly, some example embodiments may enable the provision of a BMI system that utilizes a hybrid input, shared control, and intelligent robotics to improve robotic limb control or control of other assistive devices. For example, some embodiments may enable users to visually identify an object and imagine reaching for the object to initiate a semi-autonomous reach and grasp of the object by a highly dexterous modular prosthetic limb. Physiological input signals may include eye tracking for object selection and detection of electrocorticographic (ECoG) neural responses for reach intent. System components for shared control and intelligent robotics may utilize an infrared sensor for object segmentation and semi-autonomous robotic limb control for low-level motor task planning. However, example embodiments may also be used to control other assistive devices such as, for example, wheel chairs or other household devices.

In one example embodiment, a method of controlling a device relative to one or more objects in an environment of a user employing the device is provided. The method may include receiving a volitional input from the user indicative of a task to be performed relative to an object with the device, receiving object targeting information associated with interaction between the device and the object where the object targeting information is presented in an augmented reality context, integrating the volitional input with the object targeting information to determine a control command to direct the device to interact with the object, and providing the control command to the device.

In another example embodiment, a device control unit including processing circuitry configured to control a device relative to one or more objects in an environment of a user employing the device is provided. The processing circuitry may be configured for receiving a volitional input from the user indicative of a task to be performed relative to an object with the device, receiving object targeting information associated with interaction between the device and the object where the object targeting information is presented in an augmented reality context, integrating the volitional input with the object targeting information to determine a control command to direct the device to interact with the object, and providing the control command to the device.

In accordance with another example embodiment, a system for control of a device relative to one or more objects in an environment of a user employing the device is provided. The system may include a volitional input unit, a task control unit, a targeting unit, an eye tracking unit, a machine vision unit, an integration unit and a device controller. The volitional input unit may be configured to generate trigger signals for communication to a task control unit. The trigger signals may be indicative of a task to be performed relative to an object with the device. The targeting unit may be configured to interface with an eye tracking unit and a machine vision unit to generate object targeting information associated with interaction between the device and the object. The object targeting information may be presented in an augmented reality context. The integration unit may be configured to integrate the volitional input with the object targeting information to determine a control command to direct the device to interact with the object. The device controller may be configured to receive the control command and interactively communicate with the device for closed loop control of the device based on the control command.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
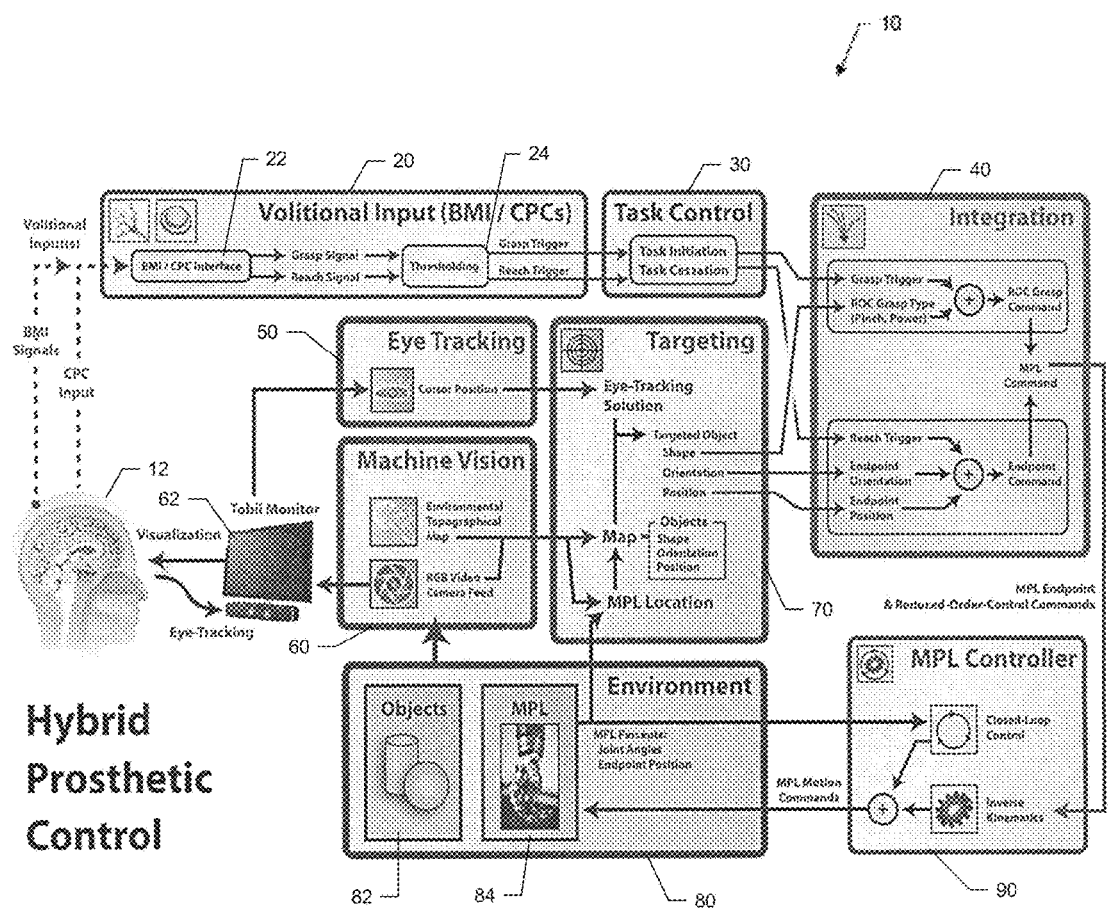
FIG. 1 illustrates a functional block diagram of a system that may be useful in connection with control of an assistive device according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

Some example embodiments may enable a relatively light hardware structure for controlling an assistive device such as, for example, a prosthetic device to be provided. Such a structure may employ a relatively small number of components that can be provided in a wearable package to provide robust control in an augmented reality environment or context. Accordingly, the control of the device afforded to the wearer and the comfort of the wearer may be enhanced. Example embodiments may be helpful when practiced with prosthetic devices, wheel chairs, household devices or other assistive devices that include grasping capabilities or other functions that would benefit from fine motor control. However, it should be appreciated that some example embodiments may alternatively be practiced in connection with other devices as well. Thus, although an example will primarily be described in a context where a user is a patient and the device is a prosthetic device, other users may also employ other devices consistent with example embodiments.

FIG. 1 is a block diagram of a system 10 for hybrid prosthetic control according to an example embodiment. As shown in FIG. 1, the system 10 may include a volitional input unit 20 and a task control unit 30. The volitional input unit 20 may include a BMI/CPC interface 22 that receives BMI signals or CPC (conventional prosthetic controls) inputs (i.e., volitional inputs from a user such as patient 12) that can be converted to reach signals or grasp signals that can be processed by a thresholding unit 24 to provide grasp trigger signals or reach trigger signals for provision to the task control unit 30. The task control unit 30 may manage task initiation and task cessation at least in part based on the grasp trigger signals or reach trigger signals. The task control unit 30 may provide inputs to an integration unit 40 that receives reach and grasp trigger information based on volitional inputs front the volitional input unit 20 via the task control unit 30.

The volitional input unit 20 and the task control unit 30 may cooperate to enable volitional inputs to be provided to initiate, modulate and discontinue automated prosthetic movements. In some cases, the volitional input unit 20 and the task control unit 30 may cooperate to generate a request for a task to be performed based on volitional inputs and queue a selected task through a context menu and enable the queued tasks to be performed. While eye tracking may also be used to initiate and discontinue tasks, volitional inputs may work in combination with the eye tracking to provide an intuitive mechanism by which users can continuously direct the prosthetic device (e.g., MPL 84) in real time. The direction of the device may include direction and modulation of a number of actions such as the speed of movement of the device, and control over closing the grasp of the device. CPC and ECoG volitional control may be employed to initiate a grasping sequence on an object detected via machine vision.

In some cases, volitional inputs may further include voice commands that can be integrated for directing tasks and prompting object recognition and task identification modules to identify and then cue predefined tasks. As an example, if a user verbally requests a task of pouring milk into a glass, the system 10 may perform machine vision aided searches for a container of milk and a glass. If matches can be found in the workspace, then a preview of the proposed task execution may be provided on a display (e.g., monitor 62) so that the patient 12 can accept the proposed plan or override the proposal and define a new trajectory or new object of interest. Additionally or alternatively, the patient 12 may be enabled to provide CPC, BMI or voice commands as volitional inputs to intuitively initiate the planned execution.

In an example embodiment, the integration unit 40 may be configured to receive control information that is integrated with the volitional inputs from an eye tracking and machine vision assembly. In this regard, an eye tracking unit 50 may be provided along with a machine vision unit 60 to provide augmented reality visualizations to the patient 12. The augmented reality visualizations may be provided via a monitor 62 that forms a part of or is otherwise in communication with the machine vision unit 60 and is visible to the patient 12.

In some cases, the monitor 62 could be provided in a pair of goggles or glasses, for example, as a transparent heads up display and, in some cases, also a machine vision element for detecting objects 82 in an environment 80 of the patient 12. The eye tracking unit 50 may interface with the monitor 62 and the patient 12 to determine where on the monitor 62 the patient 12 is looking to generate eye tracking data for communication to a targeting unit 70. The targeting unit 70 may also receive environmental topographical map or video data from the machine vision unit 60 and utilize locational information associated with objects 82 and/or an MPL 84 within the environment 80 surrounding the patient 12. MPL location, map data (which may include object shape, orientation, position and color) and/or an eye tracking solution may therefore be integrated by the targeting unit 70 to determine such information as targeted object shape, orientation, and position, which may be referred to generally as targeting information.

Accordingly, the monitor 62 may provide a tool for overlaying graphic visualizations with information and live user menus for the patient 12. As such, the monitor 62 may provide an augmented reality environment with menus that provide various modes and method of interaction for the patient 12 with the MPL 84 and objects 82 in the environment. The displayed information may inform the patient 12 in real time of the status of the MPL 84. The displayed information may also inform the patient 12 of available tasks or options for controlling the MPL 12 to interface with detected objects 82.

In addition to providing a real-time eye-tracking and machine vision capability that aids in the detecting of objects of interest to the patient 12, the monitor 62, within the context of a glasses or goggles environment, may identify the orientation and location of the patient 12 relative to objects 82. Inertial and positioning sensors may be incorporated into the system 10 to enable the orientation and location of the patient 12 and/or objects 82 to be determined. Additionally, the glasses or goggles may employ wireless sensor technology for communication with other system 10 components so that, for example, raw sensor data or other information may be streamed in real-time and processed.

The eye tracking unit 50 may be configured to align the measured user gaze location of the patient 12 with both machine vision detected objects in the environment 80 and presented context menus on the monitor 62. Thus, direct input may be provided for task control (e.g., to the integration unit 40) for high level user control that includes task identification (alignment with detected objects), and selection, initiation modulation and cessation (from context menus).

Machine vision and image processing may be employed by the machine vision unit 60 to facilitate real-time control of the MPL 84 and real-time object position determination relative to the MPL 84. Object shape and orientation information may also be determined so that, for example, strategies for approaching and grasping objects can be determined. Eye tracking may be integrated via the eye tracking unit 50 to update the monitor 62 with proposed or possible tasks. Trajectory and grasp planning may also continually be updated while tasks are being executed.

In some embodiments, the machine vision unit 60 may include sensors that can acquire both a 3D point cloud and 2D red-green-blue (RGB) raw image data of the environment. This image data may be directly streamed to the integration unit 40 (which may employ a control unit or control box) where image processing and/or segmentation may be accomplished. The image processing may include algorithms for segmenting object surfaces and extracting known features for object recognition purposes. Image processing and object recognition may be accomplished via corresponding modules in the integration unit 40, and the modules could be examples of open source or other available software libraries such as, for example, Point Cloud Library (PCL), Robot Operating System (ROS), and OpenCV. Libraries such as the examples mentioned above may be used to scale and convert images to different formats, to perform histogram calculations, to perform feature extraction, and/or to perform color based segmentation as well as 2D/3D object recognition. The libraries may also provide a software framework for implementation with a variety of machine vision sensors. Additionally or alternatively, a low cost commercial machine vision sensor technology may be employed to generate accurate 3D point clouds over long distances and with mapping resolutions that complement the expected object sizes utilized in ADL tasks.

The integration unit 40 may be configured to receive targeting information (e.g. object shape information) along with the volitional inputs and integrate such information to generate control signals for an MPL controller 90. In some embodiments, the grasp trigger signal generated based on volitional inputs may be integrated with grasp information generated by the targeting unit 70 relating to various grasp types and characteristics (e.g., pinch, power, etc.) to generate ROC (reduced order control) grasp commands. Similarly, the integration unit 40 may be configured to receive the reach trigger signals associated with volitional inputs along with targeting information (from the targeting unit 70) including endpoint orientation information and endpoint position information to generate accurate endpoint command signals. The endpoint command signals and the ROC grasp commands may combine to form MPL command signals that are provided to the MPL controller 90.

The MPL controller 90 may interface with the MPL 84 to issue MPL motion commands and to receive feedback and other information related to MPL percepts, joint angles, endpoint position and/or the like. The MPL controller 90 may provide closed loop control and employ inverse kinematics to interface with the MPL 84 based on the MPL command signals provided by the integration unit 40.

In an example embodiment, the integration unit 40 may be embodied as control or processing circuitry (as further described below in reference to FIG. 2). As such, the integration unit 40 may act as an autonomous control module for aggregating and integrating data from the task control unit 30 (i.e., volitional inputs) and the targeting unit 70 (i.e., object targeting information defining shape, size, position and orientation information about the object and indicative of resource control factors such as relative position between MPL 84 and the object) to define MPL 84 movement trajectories to perform actions outlined by a desired task. The integration unit 40 may therefore understand the environment and objects and resources therein (i.e., the location and orientation of the object to be acted upon and the nature and capabilities of the prosthetic device that will act upon the object) to perform an action based on the volitional inputs (i.e., the desired action) provided by the patient 12. The integration unit 40 may engage in planning to achieve the requested task, and the planning may take into account the object location with respect to the prosthetic and user, as well as object location, orientation, size, shape, etc., which inform the integration unit 40 as to the preferred object grasping location, wrist orientation, and coordinated finger conformations through the grasp. The hierarchical task planning and automation programming may break down high level tasks into a recipe or ordered sequence of increasingly more simple commands that are readily capable of interpretation by the MPL 84. The commands may be continually updated throughout performance of the task by integrating data from machine vision, position and velocity sensors embedded in the MPL 84 with force and contact sensors in the finger tips and hands. Continual updating of the limb trajectory can also accommodate numerous safety measures, take into account relative displacements in the object or patient 12, enhance collision avoidance, and assist with slip-detection and grasping.

Utilizing the various components or units of FIG. 1, the system 10 may provide a relatively compact product in the form of a packaged system that may be wearable and include one or more hardware elements of the system 10. The units may employ wireless communication therebetween whenever possible or appropriate. The system 10 may also include wearable glasses or goggles that integrate a display with eye tracking capabilities and machine vision technology to enable an augmented reality environment to be provided to the patient 12. The patient 12 may then interact with the augmented reality environment and also provide volitional inputs that may combine to provide a robust control over the MPL 84. Various inputs such as voice commands, BMI, CPC, or additional sensor inputs may be incorporated in a wireless communication environment to control the MPL 84. The hardware architecture and system packaging may operate via a modular software framework that is agnostic to the specific hardware employed and compatible with components produced by multiple vendors.

An example embodiment of the invention will now be described with reference to FIG. 2. FIG. 2 shows certain elements of an apparatus for provision of the data integration and prosthetic control tools described herein according to an example embodiment. The processing circuitry of the apparatus of FIG. 2 may be employed, for example, on any of the units of FIG. 1 or on a device that can control some or all of the units of FIG. 1 as individually controllable modules. However, since the integration unit 40 generally acts as the control module for the system 10, the example processing circuitry described in connection with FIG. 2 will be associated with the integration unit 40. It should be appreciated that some embodiments of the present invention may be embodied wholly at a single device, combinations of devices or by devices in a client/server relationship. Furthermore, it should be noted that the devices or elements described below may not be mandatory and thus some may be omitted in certain embodiments.

Figure 2:
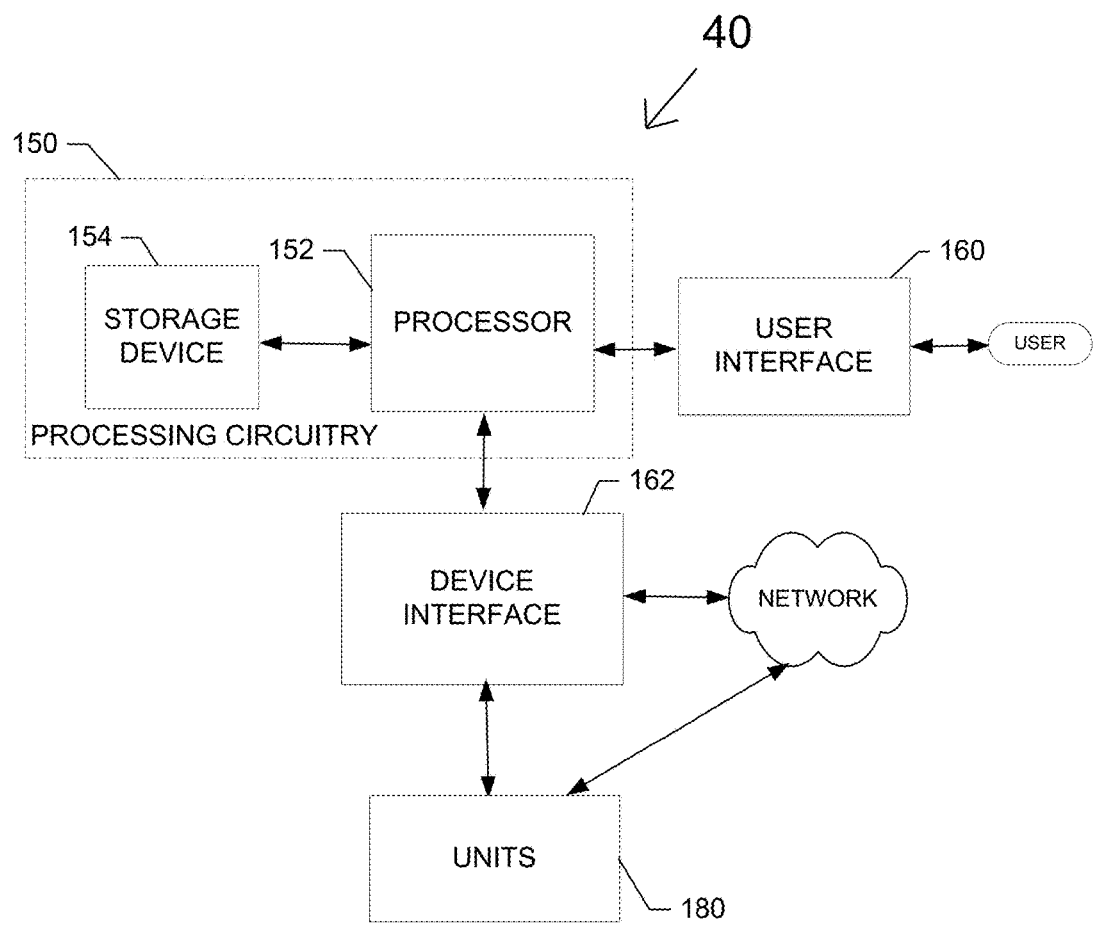
FIG. 2 illustrates a functional block diagram of an apparatus that may be useful in connection with control of the assistive device by integrating various volitional and tracking inputs according to an example embodiment.

Referring now to FIG. 2, an apparatus for provision of provision of the data integration and prosthetic control tools in accordance with an example embodiment is provided. The apparatus may be an embodiment of the integration unit 40 or a device hosting the integration unit 40. As such, configuration of the apparatus as described herein may transform the apparatus into the integration unit 40. In an example embodiment, the apparatus may include or otherwise be in communication with processing circuitry 150 that is configured to perform data processing, application execution and other processing and management services according to an example embodiment of the present invention. In one embodiment, the processing circuitry 150 may include a storage device 154 and a processor 152 that may be in communication with or otherwise control a user interface 160 and a device interface 162. As such, the processing circuitry 150 may be embodied as a circuit chip (e.g., an integrated circuit chip) configured (e.g., with hardware, software or a combination of hardware and software) to perform operations described herein. However, in some embodiments, the processing circuitry 150 may be embodied as a portion of a server, computer, laptop, workstation or even one of various mobile computing devices. In situations where the processing circuitry 150 is embodied as a server or at a remotely located computing device, the user interface 160 may be disposed at another device that may be in communication with the processing circuitry 150 via the device interface 162 and/or a network.

The user interface 160 may be in communication with the processing circuitry 150 to receive an indication of a user input at the user interface 160 and/or to provide an audible, visual, mechanical or other output to the user. As such, the user interface 160 may include, for example, a keyboard, a mouse, a joystick, a display, a touch screen, a microphone, a speaker, a cell phone, or other input/output mechanisms. In embodiments where the apparatus is embodied at a server or other network entity, the user interface 160 may be limited or even eliminated in some cases. Alternatively, as indicated above, the user interface 160 may be remotely located.

The device interface 162 may include one or more interface mechanisms for enabling communication with other devices and/or networks. In some cases, the device interface 162 may be any means such as a device or circuitry embodied in either hardware, software, or a combination of hardware and software that is configured to receive and/or transmit data from/to a network and/or any other device or module in communication with the processing circuitry 150. In this regard, the device interface 162 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 162 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 154 may include one or more non-transitory storage or memory devices such as, for example, volatile and/or non-volatile memory that may be either fixed or removable. The storage device 154 may be configured to store information, data, applications, instructions or the like for enabling the apparatus to carry out various functions in accordance with example embodiments of the present invention. For example, the storage device 154 could be configured to buffer input data for processing by the processor 152. Additionally or alternatively, the storage device 154 could be configured to store instructions for execution by the processor 152. As yet another alternative, the storage device 154 may include one of a plurality of databases that may store a variety of files, contents or data sets. Among the contents of the storage device 154, applications may be stored for execution by the processor 152 in order to carry out the functionality associated with each respective application.

The processor 152 may be embodied in a number of different ways. For example, the processor 152 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 152 may be configured to execute instructions stored in the storage device 54 or otherwise accessible to the processor 152. As such, whether configured by hardware or software methods, or by a combination thereof, the processor 152 may represent an entity (e.g., physically embodied in circuitry) capable of performing operations according to embodiments of the present invention while configured accordingly. Thus, for example, when the processor 152 is embodied as an ASIC, FPGA or the like, the processor 152 may be specifically configured hardware for conducting the operations described herein. Alternatively, as another example, when the processor 152 is embodied as an executor of software instructions, the instructions may specifically configure the processor 152 to perform the operations described herein.

In an example embodiment, the processor 152 (or the processing circuitry 150) may be embodied as, include or otherwise control the integration unit 40, which may be any means such as a device or circuitry operating in accordance with software or otherwise embodied in hardware or a combination of hardware and software (e.g., processor 152 operating under software control, the processor 152 embodied as an ASIC or FPGA specifically configured to perform the operations described herein, or a combination thereof) thereby configuring the device or circuitry to perform the corresponding functions of the integration unit 40 as described below.

The device interface 162 may enable the integration unit 40 to communicate with and/or control various other units 180, which may include the task control unit 30, the targeting unit 70, the MPL controller 90, and/or any other units of FIG. 1 or other components that are employed in connection with the system 10 of FIG. 1. Upon receiving information from various units (e.g., the task control unit 30 and the targeting unit 70), the integration unit 40 may process the received volitional inputs and object targeting information (via processing circuitry 150) and generate control signals for the MPL controller 90.

Figure 3:
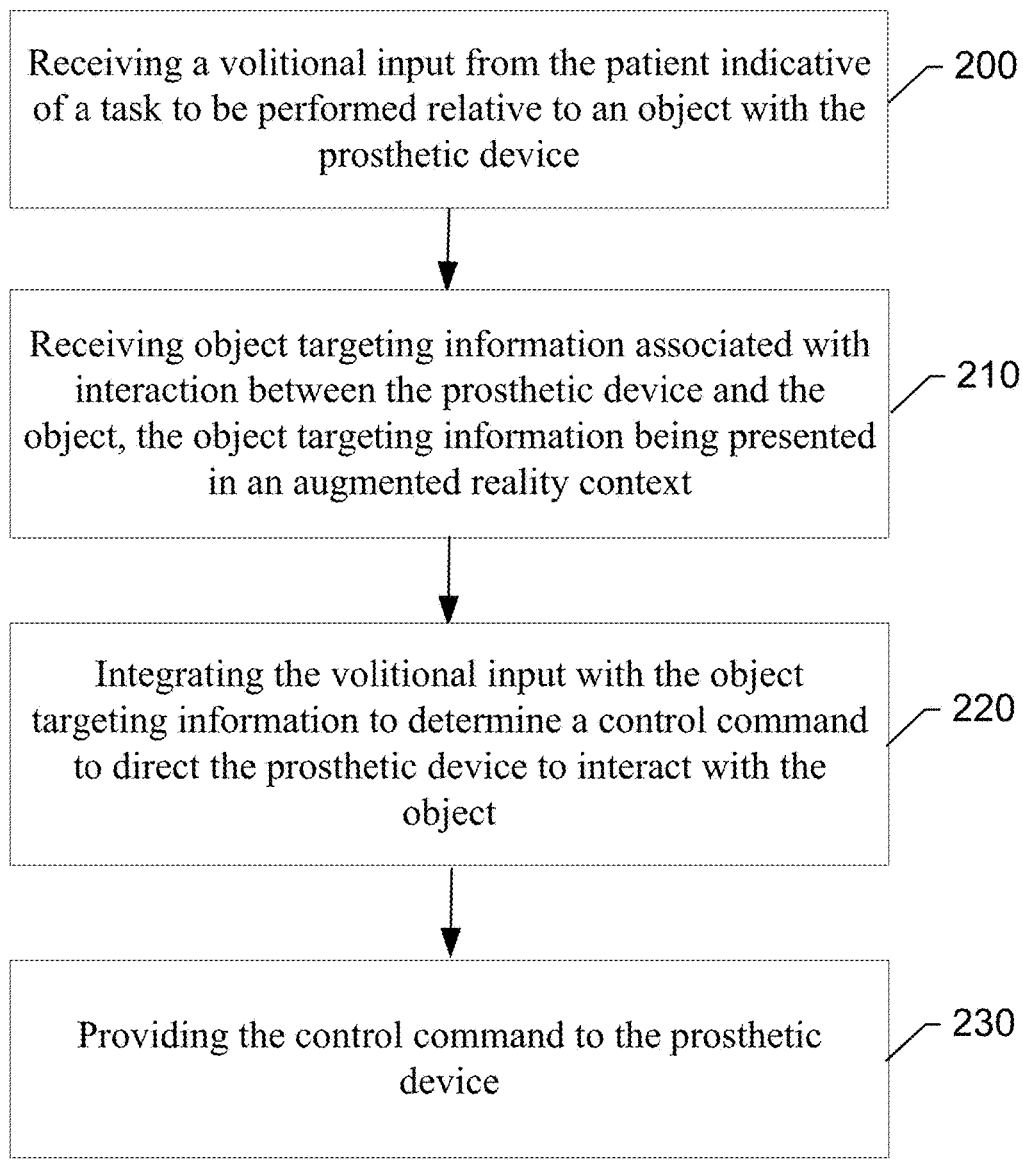
FIG. 3 illustrates a method for controlling the assistive device according to an example embodiment.

From a technical perspective, the integration unit 40 described above may be used to support some or all of the operations described above. As such, the platform described in FIGS. 1-2 may be used to facilitate the implementation of several computer program and/or network communication based interactions. As an example, FIG. 3 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal (e.g., a computer) and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method of controlling a prosthetic device relative to one or more objects in an environment of a patient employing the prosthetic device according to one embodiment of the invention, as shown in FIG. 3, may include receiving a volitional input from the patient indicative of a task to be performed relative to an object with the prosthetic device at operation 200. The method may further include receiving object targeting information associated with interaction between the prosthetic device and the object at operation 210. The object targeting information may be presented in an augmented reality context. In other words, a display of a machine vision unit may be provided to show the environment around the patient, and the display may be augmented with information that may be used to facilitate control of the prosthetic device to achieve performance of the task. In some cases, the information augmenting the display may be menu items for selection by the patient. The method may further include integrating the volitional input with the object targeting information to determine a control command to direct the prosthetic device to interact with the object at operation 220 and providing the control command to the prosthetic device at operation 230.

In an example embodiment, an apparatus for performing the method of FIG. 3 above may comprise a processor (e.g., the processor 152) or processing circuitry configured to perform some or each of the operations (200-230) described above. The processor may, for example, be configured to perform the operations (100-230) by performing hardware implemented logical functions, executing stored instructions, or executing algorithms for performing each of the operations. In some embodiments, the processor or processing circuitry may be further configured for additional operations or optional modifications to operations 200 to 230. In an example embodiment, receiving the volitional input may include receiving BMI, CPC or voice command inputs. In some embodiments, receiving the object targeting information may include receiving real-time feedback on progress toward engaging the object with the prosthetic device and updating the control command based on the feedback. Alternatively or additionally, receiving the object targeting information may include receiving information indicative of shape, size, and position of the object responsive to detection of the object via a machine vision unit associated with presentation of the augmented reality context. In some cases, receiving the object targeting information may further include receiving eye tracking information indicative of tracking a gaze of the patient relative to the object as presented by the machine vision unit. The object targeting information may be provided via goggles or glasses worn by the patient in some cases. Thus, for example, the display of the machine vision unit may be incorporated into the goggles or glasses. In some embodiments, the augmented reality context may be provided to enable a plurality of menu options to be presented to the patient via the machine vision unit. As such, for example, the patient may be enabled to select a menu option based on the volitional input or based on eye tracking in association with the machine vision unit.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A method of controlling a device relative to an environment of a user employing the device, the method comprising:

receiving a volitional input from the user indicative of a task to be performed relative to an object with the device, wherein receiving the volitional input comprises receiving brain-machine interface (BMI) command inputs;

receiving object targeting information associated with performing the task by the device, wherein the object targeting information comprises a user's eye tracking information indicative of a position of the object in a physical environment and information indicative of the position of the object in the physical environment and at least one of a size, shape, or orientation of the object as detected by a machine vision unit;

generating a control command based on a combination of the volitional input and the object targeting information, wherein the control command is configured to direct the device to interact with the object based on the task, the position, and the at least one of the size, shape, or orientation of the object; and providing the control command to the device.

2. The method of claim 1, wherein receiving the volitional input further comprises receiving conventional prosthetic control (CPC) command inputs.

3. The method of claim 1, wherein receiving the object targeting information further comprises receiving environmental information including real-time feedback on progress toward engaging the object with the device and updating the control command based on the feedback.

4. The method of claim 1, wherein the object targeting information further comprises information indicative of color or object classification with associated object weight, texture, or inertia, of the object.

5. The method of claim 1, wherein receiving the object targeting information further comprises receiving the eye tracking information at an integration unit via an eye tracking unit that interfaces with the user, wherein the eye tracking unit is configured to perform an alignment of a measured gaze location of the user's eye with a presentation of the object that has been detected using machine vision.

6. The method of claim 1, wherein receiving the object targeting information further comprises receiving the eye tracking information via goggles or glasses worn by the user.

7. The method of claim 1, the method further comprising:
outputting for presentation the representation of the object targeting information in an augmented reality context and outputting for presentation, in the augmented reality context, a plurality of menu options to be presented to the user.

8. The method of claim 1, the method further comprising:
outputting for presentation the representation of the object targeting information in an augmented reality context and outputting for presentation in the augmented reality context, a plurality of menu options to be presented to the user, and wherein the method further comprises receiving a user selection of a menu option based on eye tracking.

9. A control unit for controlling a device relative to one or more objects in an environment of a user employing the device, the control unit comprising processing circuitry configured to:
receive a volitional input from the user indicative of a task to be performed relative to an object with the device, wherein the volitional input comprises brain-machine interface (BMI) commands;
receive object targeting information associated with performing the task by the device, wherein the object targeting information comprises a user's eye tracking information indicative of a position of the object in a physical environment and information indicative of the position of the object in the physical environment and at least one of a size, shape, or orientation of the object as detected by a machine vision unit;
generate a control command based on a combination of the volitional input and the object targeting information, wherein the control command is configured to direct the device to interact with the object based on the task, the position, and the at least one of the size, shape, or orientation of the object; and
provide the control command to the device.

10. The control unit of claim 9, wherein the processing circuitry configured to receive the volitional input is further configured to receive voice command inputs or conventional prosthetic control (CPC) command inputs.

11. The control unit of claim 9, wherein the processing circuitry configured to receive the object targeting information is further configured to receive real-time feedback on progress toward engaging the object with the device and updating the control command based on the feedback.

12. The control unit of claim 9, wherein the processing circuitry configured to receive the object targeting information includes being configured to receive the object targeting information further comprising information indicative of color or object classification with associated object weight, texture, or inertia, of the object responsive as detected by the machine vision unit.

13. The control unit of claim 9, wherein the processing circuitry configured to receive the object targeting information is further configured to receive the eye tracking information at an integration unit via an eye tracking unit that interfaces with the user, wherein the eye tracking unit is configured to perform an alignment of a measured gaze location of the user's eye with a presentation of the object that has been detected using machine vision.

14. The control unit of claim 9, wherein the processing circuitry configured to receive the object targeting information is further configured to receive the eye tracking information via goggles or glasses worn by the user.

15. The control unit of claim 9, wherein the processing circuitry is further configured to:
output for presentation the representation of the object targeting information and output for presentation, in an augmented reality context, a plurality of menu options to be presented to the user.

16. The control unit of claim 9, wherein the processing circuitry is further configured to:
output for presentation the representation of the object targeting information and output for presentation in an augmented reality context a plurality of menu options to be presented to the user, and wherein the processing circuitry is further configured to receive a user selection of a menu option based on eye tracking.

17. A system for control of a device relative to one or more objects in an environment of a user employing the device, the system comprising:
a volitional input unit configured to receive a volitional input comprising brain-machine interface (BMI) command inputs and, in response to receiving the volitional input, generate trigger signals for communication to a task control unit, the trigger signals indicative of a task to be performed relative to an object by the device;
a targeting unit configured to interface with an eye tracking unit and a machine vision unit, the targeting unit being further configured to:
receive object targeting information associated with performing the task by the device, wherein the object targeting information comprises a user's eye tracking information provided by the eye tracking unit and information indicative of a position of the object in a physical environment and at least one of a size, shape, or orientation of the object as detected by the machine vision unit; and output a representation of the object targeting information in an augmented reality context;

an integration unit configured to generate a control command based on a combination of the volitional input with the object targeting information, wherein the control command directs the device to interact with the object based on the task, the position, and the at least one of the size, shape, or orientation of the object; and a device controller configured to receive the control command and interactively communicate with the device for closed loop control of the device based on the control command.

18. The system of claim 17, wherein the volitional input unit is further configured to receive voice command inputs, and wherein the targeting unit is further configured to generate object targeting information comprising real-time feedback on progress toward engaging the object with the device.

19. The system of claim 17, wherein the targeting unit is further configured to receive eye tracking information from the eye tracking unit, the eye tracking unit being configured to perform alignment of a measured gaze location of the user's eye with a presentation of the object that has been detected using machine vision.

20. The system of claim 17, wherein the targeting unit configured to output the representation of the object targeting information includes being configured to output, in the augmented reality context, a plurality of menu options to be presented to the user, and wherein the targeting unit is further configured to receive a user selection of a menu option based on eye tracking.

* * * * *